United States Patent
Hamed

(10) Patent No.: US 8,927,025 B2
(45) Date of Patent: *Jan. 6, 2015

(54) ALCOHOL-RESISTANT METOPROLOL-CONTAINING EXTENDED-RELEASE ORAL DOSAGE FORMS

(75) Inventor: Ehab Hamed, Concord, MA (US)

(73) Assignee: Cima Labs Inc., Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/721,128

(22) PCT Filed: May 9, 2011

(86) PCT No.: PCT/US2011/035770
§ 371 (c)(1), (2), (4) Date: May 6, 2013

(87) PCT Pub. No.: WO2011/143120
PCT Pub. Date: Nov. 17, 2011

(65) Prior Publication Data
US 2013/0266660 A1  Oct. 10, 2013

Related U.S. Application Data

(60) Provisional application No. 61/333,531, filed on May 11, 2010.

(51) Int. Cl.
A61K 9/16 (2006.01)
A61K 9/20 (2006.01)
A61K 31/135 (2006.01)

(52) U.S. Cl.
CPC ............... *A61K 9/16* (2013.01); *A61K 9/2022* (2013.01); *A61K 9/2027* (2013.01); *A61K 9/2054* (2013.01); *A61K 31/135* (2013.01)
USPC ........... 424/495; 424/490; 424/493; 424/494; 424/497; 514/652

(58) Field of Classification Search
None
See application file for complete search history.

(56) References Cited

U.S. PATENT DOCUMENTS

| | | |
|---|---|---|
| 4,814,176 A | 3/1989 | Makino et al. |
| 4,844,909 A | 7/1989 | Goldie et al. |
| 4,861,598 A | 8/1989 | Oshlack |
| 4,863,456 A | 9/1989 | Stephens et al. |
| 4,873,092 A | 10/1989 | Azuma et al. |
| 4,970,075 A | 11/1990 | Oshlack |
| 4,990,341 A | 2/1991 | Goldie et al. |
| 5,133,974 A | 7/1992 | Paradissis et al. |
| 5,169,645 A | 12/1992 | Shukla et al. |
| 5,178,878 A | 1/1993 | Wehling et al. |
| 5,266,331 A | 11/1993 | Oshlack et al. |
| 5,273,760 A | 12/1993 | Oshlack et al. |
| 5,286,493 A | 2/1994 | Oshlack et al. |
| 5,321,012 A | 6/1994 | Mayer et al. |
| 5,352,683 A | 10/1994 | Mayer et al. |
| 5,403,593 A | 4/1995 | Royce |
| 5,445,829 A | 8/1995 | Paradissis et al. |
| 5,458,879 A | 10/1995 | Singh et al. |
| 5,460,828 A | 10/1995 | Santus et al. |
| 5,472,712 A | 12/1995 | Oshlack et al. |
| 5,478,577 A | 12/1995 | Sackler et al. |
| 5,500,227 A | 3/1996 | Oshlack et al. |
| 5,503,846 A | 4/1996 | Wehling et al. |
| 5,508,042 A | 4/1996 | Oshlack et al. |
| 5,549,912 A | 8/1996 | Oshlack et al. |
| 5,580,578 A | 12/1996 | Oshlack et al. |
| 5,593,694 A | 1/1997 | Hayashida et al. |
| 5,614,218 A | 3/1997 | Olsson et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,731,006 A | 3/1998 | Akiyama et al. |
| 5,744,166 A | 4/1998 | Illum et al. |
| 5,811,126 A | 9/1998 | Krishnamurthy et al. |
| 5,840,754 A | 11/1998 | Guittard et al. |
| 5,849,240 A | 12/1998 | Miller et al. |
| 5,851,555 A | 12/1998 | Sanghvi et al. |

(Continued)

FOREIGN PATENT DOCUMENTS

| | | |
|---|---|---|
| EP | 0311582 | 4/1989 |
| EP | 1419766 | 5/2004 |

(Continued)

OTHER PUBLICATIONS

Brendenberg "New Concepts in Administration of Drugs in Tablet Form: Formulation and Evaluation of a Sublingual Tablet for Rapid Absorption and Presentation of an Individualized Dose Administration System Acta Universitatis Upsaliensis." *Comprehensive Summaries of Uppsala Dissertations from the Faculty of Pharmacy* 287 83 pp. Uppsala ISBN 91-554-5600-6 (2003).

Frohof-Hulsmann et al., "Aqueous Ethyl Cellulose Dispersion Containing Plasticizers of Different Water Solubility and Hydroxypropyl Methyl-Cellulose as Coating Material for Diffusion Pellets II: Properties of Sprayed Films", European Journ. Of Pharma and Biopharma., vol. 48, pp. 67-75, 1999.

Gustafsson et al., "Characterisation of Particle Properties and Compaction Behaviour of Hydroxypropyl Methylcellulose with Different Degrees of Methoxy/Hydroxypropyl Substitution", EP Journ of Pharmaceutical Sci. 9, pp. 171-184, 1999.

Hyppola et al., "Evaluation of Physical Properties of Plasticized Ethyl Cellulose Films Cast From Ethanol Solution Part I", International Journ. of Pharma., vol. 133, pp. 161-170, 1996.

(Continued)

*Primary Examiner* — Suzanne Ziska
*Assistant Examiner* — Thurman Wheeler

(57) ABSTRACT

This disclosure relates to an extended release oral dosage form comprising a matrix containing a viscosity modifier (but no lipid) and coated granules containing metoprolol or a pharmaceutically acceptable salt or solvate thereof. The dosage form has alcohol resistance and may also have crush resistance.

5 Claims, 2 Drawing Sheets

(56) References Cited

U.S. PATENT DOCUMENTS

| | | | |
|---|---|---|---|
| 5,858,412 A | 1/1999 | Staniforth et al. |
| 5,891,471 A | 4/1999 | Miller et al. |
| 5,904,927 A | 5/1999 | Amiji |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 5,968,661 A | 10/1999 | Saito et al. |
| 6,024,981 A | 2/2000 | Khankari et al. |
| 6,039,980 A | 3/2000 | Baichwal |
| 6,103,219 A | 8/2000 | Sherwood et al. |
| 6,103,261 A | 8/2000 | Chasin et al. |
| 6,129,933 A | 10/2000 | Oshlack et al. |
| 6,143,322 A | 11/2000 | Sackler et al. |
| 6,143,353 A | 11/2000 | Oshlack et al. |
| 6,155,423 A | 12/2000 | Katzner et al. |
| 6,159,501 A | 12/2000 | Skinhoj et al. |
| 6,162,467 A | 12/2000 | Miller et al. |
| 6,194,005 B1 | 2/2001 | Farah et al. |
| 6,200,604 B1 | 3/2001 | Pather et al. |
| 6,228,398 B1 | 5/2001 | Devane et al. |
| 6,238,704 B1 | 5/2001 | Suzuki et al. |
| 6,245,351 B1 | 6/2001 | Nara et al. |
| 6,245,357 B1 | 6/2001 | Edgren et al. |
| 6,251,430 B1 | 6/2001 | Zhang et al. |
| 6,261,599 B1 | 7/2001 | Oshlack et al. |
| 6,290,990 B1 | 9/2001 | Grabowski et al. |
| 6,294,195 B1 | 9/2001 | Oshlack et al. |
| 6,309,668 B1 | 10/2001 | Bastin et al. |
| 6,316,031 B1 | 11/2001 | Oshlack et al. |
| 6,335,033 B2 | 1/2002 | Oshlack et al. |
| 6,368,625 B1 | 4/2002 | Siebert et al. |
| 6,375,987 B1 | 4/2002 | Farah et al. |
| 6,387,404 B2 | 5/2002 | Oshlack et al. |
| 6,399,096 B1 | 6/2002 | Miller et al. |
| 6,419,954 B1 | 7/2002 | Chu et al. |
| 6,500,459 B1 | 12/2002 | Chhabra et al. |
| 6,534,091 B1 | 3/2003 | Garces et al. |
| 6,572,885 B2 | 6/2003 | Oshlack et al. |
| 6,589,960 B2 | 7/2003 | Harclerode et al. |
| 6,680,071 B1 | 1/2004 | Johnson et al. |
| 6,685,964 B1 | 2/2004 | Bartholomäus et al. |
| 6,699,502 B1 | 3/2004 | Fanara et al. |
| 6,706,281 B2 | 3/2004 | Oshlack et al. |
| 6,730,321 B2 | 5/2004 | Ting et al. |
| 6,730,325 B2 | 5/2004 | Devane et al. |
| 6,733,783 B2 | 5/2004 | Oshlack et al. |
| 6,733,790 B1 | 5/2004 | Garces et al. |
| 6,743,442 B2 | 6/2004 | Oshlack et al. |
| 6,753,014 B1 | 6/2004 | Sjoblom et al |
| 6,759,059 B1 | 7/2004 | Pettersson et al. |
| 6,780,504 B2 | 8/2004 | Rupprecht et al. |
| 6,793,936 B2 | 9/2004 | Devane et al. |
| 6,863,901 B2 | 3/2005 | Hirsh et al. |
| 6,902,742 B2 | 6/2005 | Devane et al. |
| 6,905,709 B2 | 6/2005 | Oshlack et al. |
| 7,022,313 B2 | 4/2006 | O'Connor et al. |
| 7,090,867 B2 | 8/2006 | Odidi et al. |
| 7,387,792 B2 | 6/2008 | Hirsh et al. |
| 7,399,488 B2 | 7/2008 | Hirsh et al. |
| 7,514,100 B2 | 4/2009 | Oshlack et al. |
| 7,658,939 B2 | 2/2010 | Oshlack et al. |
| 7,776,314 B2 | 8/2010 | Bartholomäus et al. |
| 2002/0044966 A1 | 4/2002 | Bartholomäus et al. |
| 2002/0110595 A1 | 8/2002 | Chang et al. |
| 2002/0110598 A1 | 8/2002 | Chung et al. |
| 2003/0077297 A1 | 4/2003 | Chen et al. |
| 2003/0180362 A1 | 9/2003 | Park et al. |
| 2003/0190358 A1 | 10/2003 | Oshlack et al. |
| 2004/0009219 A1 | 1/2004 | Odidi et al. |
| 2004/0028735 A1 | 2/2004 | Kositprapa |
| 2004/0052844 A1 | 3/2004 | Hsiao et al. |
| 2004/0096499 A1 | 5/2004 | Vaya et al. |
| 2004/0096500 A1 | 5/2004 | Oshlack et al. |
| 2004/0105887 A1 | 6/2004 | Oshlack et al. |
| 2004/0121001 A1 | 6/2004 | Oshlack et al. |
| 2004/0131552 A1 | 7/2004 | Boehm |
| 2004/0142035 A1 | 7/2004 | Chang et al. |
| 2004/0151791 A1 | 8/2004 | Mayo-Alvarez et al. |
| 2004/0157784 A1 | 8/2004 | Chopdekar et al. |
| 2004/0170680 A1 | 9/2004 | Oshlack et al. |
| 2004/0185098 A1 | 9/2004 | Oshlack et al. |
| 2004/0208930 A1 | 10/2004 | Yoneda et al. |
| 2004/0208936 A1 | 10/2004 | Chorin et al. |
| 2004/0224017 A1 | 11/2004 | Mulye |
| 2004/0253310 A1 | 12/2004 | Fischer et al. |
| 2005/0020613 A1 | 1/2005 | Boehm et al. |
| 2005/0053656 A1 | 3/2005 | Ping |
| 2005/0074493 A1 | 4/2005 | Mehta et al. |
| 2005/0089568 A1 | 4/2005 | Oshlack et al. |
| 2005/0106249 A1 | 5/2005 | Hwang et al. |
| 2005/0163856 A1 | 7/2005 | Maloney et al. |
| 2005/0165038 A1 | 7/2005 | Gordon |
| 2005/0169989 A1 | 8/2005 | Moe et al. |
| 2005/0169990 A1 | 8/2005 | Kao et al. |
| 2005/0245483 A1 | 11/2005 | Brogmann et al. |
| 2005/0266072 A1 | 12/2005 | Oshlack et al. |
| 2006/0024361 A1 | 2/2006 | Odidi et al. |
| 2006/0104909 A1 | 5/2006 | Vaghefi et al. |
| 2006/0153915 A1 | 7/2006 | Park et al. |
| 2006/0153916 A1 | 7/2006 | Vaya et al. |
| 2006/0204573 A1 | 9/2006 | Mulye |
| 2006/0233879 A1 | 10/2006 | Lerner et al. |
| 2006/0233880 A1 | 10/2006 | Lerner et al. |
| 2006/0251721 A1 | 11/2006 | Cruz et al. |
| 2006/0263429 A1 | 11/2006 | Feng |
| 2006/0269604 A1 | 11/2006 | Sackler et al. |
| 2007/0003671 A1 | 1/2007 | Fischer et al. |
| 2007/0009589 A1* | 1/2007 | Raghupathi et al. ......... 424/451 |
| 2007/0009598 A1 | 1/2007 | Marechal et al. |
| 2007/0020335 A1 | 1/2007 | Chen et al. |
| 2007/0203165 A1 | 8/2007 | Shafer et al. |
| 2007/0212414 A1 | 9/2007 | Baichwal et al. |
| 2007/0231268 A1 | 10/2007 | Emigh et al. |
| 2008/0069891 A1 | 3/2008 | Habib |
| 2009/0238868 A1 | 9/2009 | Mehta |
| 2009/0297617 A1 | 12/2009 | Rariy et al. |
| 2009/0304793 A1 | 12/2009 | Boehm |
| 2009/0317355 A1 | 12/2009 | Roth et al. |
| 2010/0015223 A1 | 1/2010 | Cailly-Dufestel et al. |
| 2010/0098771 A1 | 4/2010 | Mehta |

FOREIGN PATENT DOCUMENTS

| | | |
|---|---|---|
| EP | 1504757 | 2/2005 |
| EP | 1782834 | 5/2007 |
| WO | WO9939698 | 8/1999 |
| WO | WO0236099 | 5/2002 |
| WO | WO02092059 | 11/2002 |
| WO | WO2004026256 | 4/2004 |
| WO | WO2004064807 | 8/2004 |
| WO | WO2004084865 | 10/2004 |
| WO | WO2004093819 | 11/2004 |
| WO | WO2004108117 | 12/2004 |
| WO | WO2005034930 | 4/2005 |
| WO | WO2005099674 | 10/2005 |
| WO | WO2007048233 | 5/2007 |
| WO | WO2007103293 | 9/2007 |
| WO | WO2007112574 | 10/2007 |
| WO | WO2008140460 | 11/2008 |
| WO | WO2009036812 | 3/2009 |
| WO | WO2009059701 | 5/2009 |
| WO | WO2010033195 | 3/2010 |

OTHER PUBLICATIONS

International Preliminary Report on Patentability and Written Opinion re: PCT/US2011/035767 dated Nov. 13, 2012.
International Preliminary Report on Patentability and Written Opinion re: PCT/US2011/035768 dated Nov. 22, 2012.
International Preliminary Report on Patentability and Written Opinion re: PCT/US2011/035770 dated Nov. 22, 2012.
International Preliminary Report on Patentability and Written Opinion re: PCT/US2011/025914 dated Sep. 7, 2012.

(56) References Cited

OTHER PUBLICATIONS

International Search Report and Written Opinion for PCT/US2007/020041, dated Feb. 25, 2008.

Physician's Desk Reference 57th ed. 2003 p. 1184 (package insert information for ACTIQ).

Portenoy et al. "Fentanyl Buccal Tablet (FBT) for Relief of Breakthrough Pain in Opioid-Treated Patients with Chronic Low Back Pain: A Randomized, Placebo-Controlled Study", ASRA 06, Final Abstract, Submitted Aug. 4.

Portenoy et al. "Fentanyl Buccal Tablet (FBT) for Relief of Breakthrough Pain in Opioid-Treated Patients with Chronic Low Back Pain", Current Medical Research and Opinion, vol. 23(7), pp. 223-233, 2007.

Siepmann et al., "A New Model Describing the Swelling and Drug Release Kinetics from Hydroxypropyl Methylcellulose Tablets", Journ. of Pharmaceutical Sciences, vol. 88, No. 1, pp. 65-72, Jan. 1999.

Sung et al., "Effect of Formulation Variables on Drug and Polymer Release from HPMC-Based Matrix Tablets", International Journ. Of Pharmaceutics vol. 142, pp. 53-60, 1996.

Vashi et al., "Clinical Pharmacology and Pharmacokinetics of Once-Daily Hydromorphone Hydrochloride Extended-Release Capsules", J. Clin. Pharmacol, vol. 45, pp. 547-554, 2005.

Viriden et al., "Investigation of Critical Polymer Properties for Polymer Release and Swelling of HPMC Matrix Tablets", EP Journal of Pharmaceutical Sciences 36, pp. 297-309, 2009.

Webster, "PTI-821: Sustained-Release Oxycodone Using Gel-Cap Technology", Expert Opin. Investig. Drugs, vol. 16, (3), pp. 1-8, 2007.

* cited by examiner

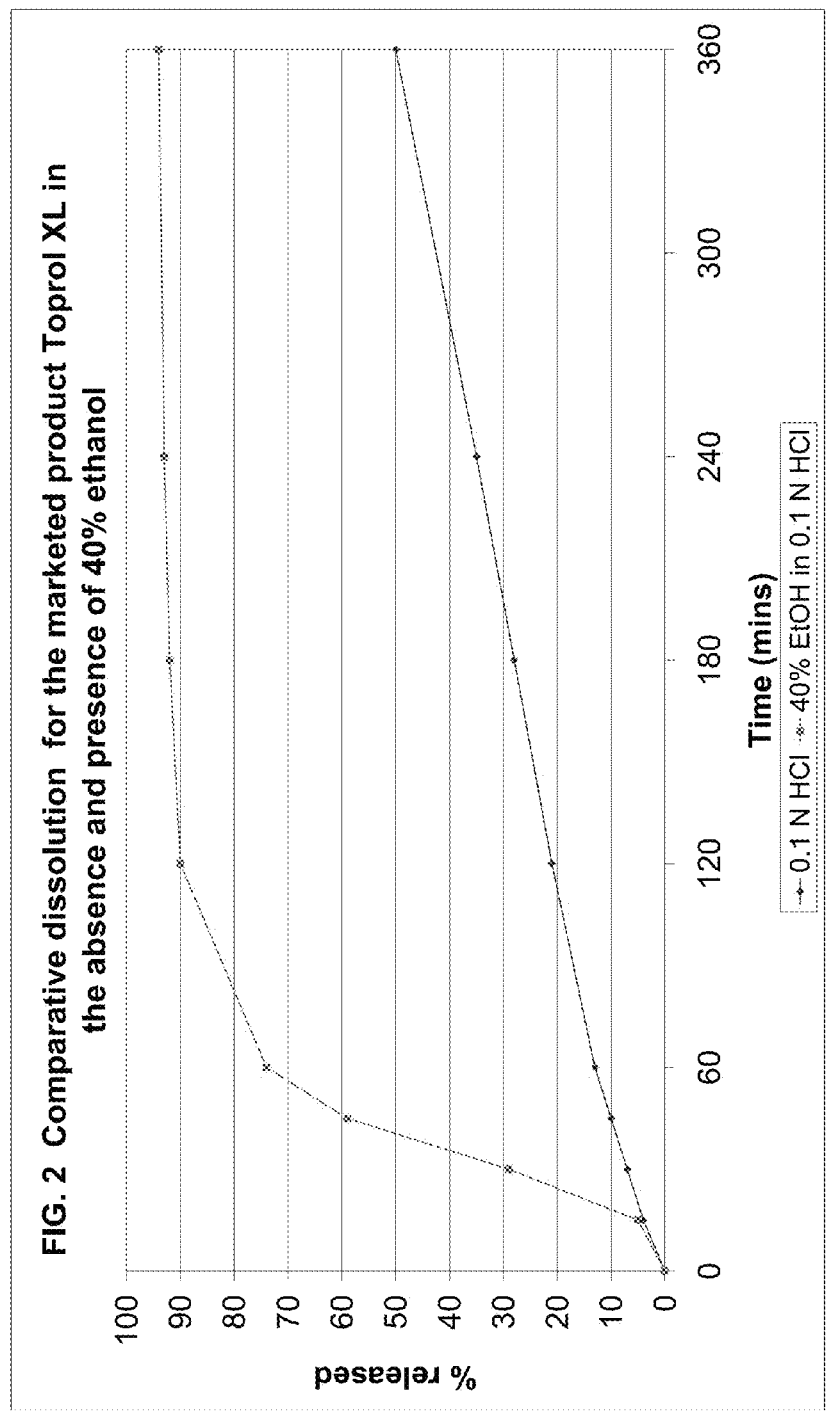

ALCOHOL-RESISTANT METOPROLOL-CONTAINING EXTENDED-RELEASE ORAL DOSAGE FORMS

CROSS REFERENCE TO RELATED APPLICATIONS

This application claims the benefit of the filing date of International Patent Application Serial No. PCT/US2011/35770, filed May 9, 2011, which claims priority to U.S. Provisional Patent Application No. 61/333,531 filed May 11, 2010, the disclosure of which is hereby incorporated by reference in its entirety.

TECHNICAL FIELD

This invention relates to non-lipid matrix based alcohol-resistant extended release dosage forms of metoprolol and pharmaceutically acceptable salts and solvates (e.g. hydrates) thereof.

BACKGROUND

Orally administered drugs are typically formulated into tablets or capsules. For most drugs, to maintain the drug level in the body above the minimal therapeutically effective level, these dosage forms are administered frequently (every 4 hr, 6 hr, 8 hr etc). Such administration schedule can lead to patience non-compliance and therapeutic complication due to repeated incidence of missed doses, especially when the patient is administering multiple drugs. To address this issue, drugs are formulated into extended release dosage forms, where multiple doses are combined into the dosage form to be released over an extended period of time, thereby reducing the dosing frequency to once or twice daily.

While there are several approaches to extend the drug release from orally administered dosage forms, they can be generally classified to reservoir or matrix systems [Colombo et al., 2008, Swellable and Rigid Matrices: Controlled Release Matrices with Cellulose Ethers. In: Pharmaceutical Dosage Forms: Tablets, Volume 2: Rational Design and Formulation. Third Edition, Augsburger, L. and Hoag, S. (eds.). Informa Healthcare, New York, London]. Reservoir systems are based on coating a drug loaded core with water insoluble polymers or lipids through which drug diffusion is slow. Matrix systems are based on using either plastic or gelling materials to form tortuous or highly viscous matrices respectively. The increased tortuosity or viscosity leads to slower drug diffusion and hence slower release from the dosage form. For both systems, the amount of release-extending excipient used is dictated by several factors, most notably the drug solubility, dose and the intended release rate. For highly water-soluble drugs, a high level of release-extending excipient is required in addition to other excipients, such as binders and lubricants, needed to form robust tablets. The requirement for a high excipient load makes formulating high dose drugs particularly challenging since it is difficult to maintain the final dosage form size within a suitable range for swallowing, e.g. 1 gram or less.

Another challenge for formulating an extended release dosage form for drugs with high dose and high aqueous solubility is the susceptibility of the release-extending elements to alcohol induced dose-dumping which can be fatal. For example, in 2005, the FDA requested the manufacturer of once-daily hydromorphone extended release capsules to suspend its product sales citing serious and potentially fatal adverse reactions that occurred when the product was taken together with alcohol. Several of the pharmaceutical grade excipients used to control drug release are soluble in alcohol rendering the corresponding dosage form susceptible to alcohol induced dose-dumping. These excipients include, but are not limited to, ethyl cellulose, polyethylene glycol, poly(oxyethylene, oxypropylene), poly(methacrylic acid, methyl methacrylate), poly(methacrylic acid, ethyl acrylate), poly(ethyl acrylate, methyl methacrylate, trimethylammonioethyl methacrylate chloride), poly(butyl methacrylate, 2-dimethylaminoethyl methacrylate, methyl methacrylate), cetosteryl alcohol, polyvinyl acetate phthalate and shellac.

Due to the alcohol susceptibility of many of the pharmaceutical grade excipients, formulators have resorted to using lipid matrices to extend the drug release and impart alcohol resistance owing to the insolubility of most lipids in alcohol or hydroalcoholic solvents. However, using lipids matrices to extend drug release carries several disadvantages including:

1. Physical and chemical instability of the lipids. Most lipids are prone to rancidity on storage via a complex free radical reaction (Craig, D. Q. M., 2004. Lipid Matrices for Sustained Release-An Academic Review. Bulletin Technique Gattefosse No 97).
2. Nearly all lipids are also prone to physical state transformation (polymorphic transition, crystallization and/or amorphization) which can affect the dosage forms characteristics and performance (Souto, E. B., Menhert, W., Muller, R. H., 2006. Polymorphic behavior of Compritol®888 ATO as bulk lipid and as SLN and NLC. J. Microencaps. 23(4), 417-433. Hamadani, J., Moes, A. J., Amighi, K., 2003. Physical and thermal characterization of Precirol® and Compritol® as lipophilic glycerides used for the preparation of controlled release matrix pellets. Int. J. Pharm., 260, 47-57).
3. Lipid based extended release dosage forms are prone to in vitro dissolution profiles changes on aging (Khan, N and Craig, D. Q. M., 2004. The role of blooming in determining the storage stability of lipid based dosage forms. J. Pharm. Sci., 93, 2962-2971. Choy, Y. W., Nurzaline Khan, Yuen, K. H., 2005. Significance of lipid matrix aging on in vitro release and in vivo bioavailability. Int. J. Pharm., 299, 55-64. San Vicente, A., Hernandez, R. M., Gascon, A. R., Calvo, M. B., Pedraz, J. L., 2000. Effect of aging on the release of salbutamol sulfate from lipid matrices. Int. J. Pharm, 208, 13-21).
4. Simple dosage form manufacturing processes such as tablet and capsule filling are not easily applicable to many lipid systems (Craig, D. Q. M., 2004. Lipid Matrices for Sustained Release-An Academic Review. Bulletin Technique Gattefosse No 97).
5. Extended release dosage forms based on lipidic matrices are more prone to food effect compared to other dosage forms owing to the increased secretion of digestive enzymes with food that affect the integrity of the dosage form.
6. The dependence of the dosage form integrity and hence the release characteristics on the effect of gastrointestinal enzymes caused lipid-based dosage forms to show more inter- and intra-individual variability (Craig, D. Q. M., 2004. Lipid Matrices for Sustained Release-An Academic Review. Bulletin Technique Gattefosse No 97).

Metoprolol is a selective beta 1-adrenoreceptor blocking agent used to treat hypertension, angina pectoris and myocardial infarction. It is approved in the US in three salt forms, namely the succinate, fumarate and tartrate, where all dosages are calculated in equivalence to the tartrate salt. It is available as immediate release oral tablets (25, 50 and 100 mg equivalent to the tartrate salt), extended release oral tablets or capsules for once daily administration (25, 50, 100, 200, 300 and 400 mg equivalent to the tartrate salt) as well as in ampoules for intravenous injection (1 mg/ml). Both the tartrate and succinate salts are highly soluble in water. The high water solubility and the high dose needed for extended release dosage pose significant challenges to formulating metoprolol salts as alcohol resistant extended release formulations.

The current invention aims to address the above challenges by formulating metoprolol and pharmaceutically acceptable salts (e.g. the tartrate or succinate salt) and solvates (e.g. hydrates) into an alcohol resistant extended release dosage form without resorting to the use of lipids.

SUMMARY

Non-lipid matrix based alcohol-resistant extended release dosage forms of metoprolol and pharmaceutically acceptable salts and solvates thereof are provided. More particularly, the present invention related to alcohol-resistant extended release dosage forms of metoprolol and pharmaceutically acceptable salts (e.g. the succinate or tartrate salt) and solvates (e.g. hydrates) comprising a matrix containing a viscosity modifier (but no lipid component) and coated granules comprising a highly water-soluble drug present in high dose.

As described herein, dosages that are extended release, such as once-a-day, or twice a day, typically contain a larger concentration of pharmaceutically active ingredients. Such larger concentrations of pharmaceutically active ingredients make the dosage forms more dangerous, especially if the dosage forms are susceptible to dumping the pharmaceutically active ingredients (releasing an undesirable high concentration of the active ingredient in a short amount of time) when they are crushed, taken with alcohol, and/or are taken with food. Therefore, dosage forms that are resistant to one or more causes of dose dumping are desirable.

"Non-lipid matrix based" describes an alcohol-resistant extended release dosage form that can additionally be resistant to food effect, which does not contain a lipid within the matrix component of said dosage form. Dosage forms that are resistant to food effect, meaning that the $C_{max}$ of the dosage form will not change more than 50%, 45%, 40%, or 35% when it is consumed with food vs. without food. One of ordinary skill in the art will appreciate that formulations that are resistant to food effect are generally safer, because their safety is not as reliant upon patient compliance.

As described herein, references to "lipid" mean hydrophobic compounds generally having a hydrophilic/lipophilic balance (HLB) of about 6 or less and also having a melting point which is 30° C. or more. The term can be used interchangeably with fat or wax if they meet the same specifications. Lipids can be fatty acids, fatty alcohol, fatty esters or wax. The fatty acids can be substituted or unsubstituted, saturated or unsaturated. However, generally they have a chain length of at least about 14 carbon atoms. The fatty esters may include fatty acid bound to alcohols, glycols or glycerol to form mono-, di-, and tri-fatty substituted esters. Examples include, glycerol fatty esters, fatty glyceride derivatives, and fatty alcohols such as glycerol behenate (COMPRITOL®), glycerol palmitostearate (PRECIROL®), stearoyl macroglycerides (GELUCIRE®), insect and animal waxes, vegetable waxes, mineral waxes, petroleum waxes, and synthetic waxes.

In one embodiment, a dosage form, as described herein, has a release profile such that after 6 hours in 500 ml of 0.1N hydrochloric acid, less than about 80 percent of the drug is released.

In addition, a dosage form, as described herein, has alcohol resistance and may have crush resistance. Thus, in another embodiment, the percent of drug released after 2 hours in a solution of 0.1N hydrochloric acid and 40% alcohol is no more than 10 percentage points greater than the percent of the same drug released in a solution of 0.1N hydrochloric acid in the absence of alcohol. In some embodiments, the release of drug from the dosage form 30 minutes after simulated oral tampering is less than about 50 percent.

The dosage form may be also resistant to food effect. Generally, resistance to food effect is identified by comparing pharmacokinetic parameters from subjects that are fasted to those that have consumed a standard diet. In some situations a standard diet can be high fat (i.e., about 50% of the calories are from fat), high carbohydrate or any other standard diet. A dosage form that is resistant to food effect (i.e., a % change in pharmacokinetic parameters comparing fasted and fed states) will show a smaller % change in pharmacokinetic parameters, such as $C_{max}$, $T_{max}$, or $A_{uc}$ at various time points when compared to other dosage forms. For example, a formulation may show a 0% change in $T_{max}$ between the fed and fasted data and therefore, be classified as resistant to food effect. However, a different formulation may show a 60% change in $T_{max}$ between the fed and fasted data. Thus, the formulation that showed a 60% change is less resistant to food effect than the formulation that displayed a 0% change in $T_{max}$. In some instances the percent change in $T_{max}$ will be less than 50%, 45%, 40%, 35%, 30%, 20%, 15% depending upon the formulation and its resistance to food effect.

In some embodiments, when tested in a group of at least five fasted healthy humans and compared to a group of at least 5 fed humans, as described herein, the % change of the mean $C_{max}$ will be less than about 50%, 45%, 40%, 30%, 25%, 20%, or 15%. The concentration of active pharmaceutical ingredient human plasma samples can be measured using any method known in the art, for example when testing opioids a validated high-performance liquid chromatography method with tandem mass spectrometric detection (LC-MS/MS) can be used.

In one particular embodiment of the invention we provide herein an alcohol-resistant extended release dosage form of metoprolol or a pharmaceutically acceptable salt or solvate thereof comprising: a matrix, wherein the matrix comprises a viscosity modifier in an amount from about 1 to about 60 percent by weight of the dosage form; and coated granules comprising said metoprolol or a pharmaceutically acceptable salt or solvate thereof; and wherein the matrix does not contain a lipid.

In another embodiment we provide an alcohol-resistant extended release dosage form for once-daily administration of metoprolol or a pharmaceutically acceptable salt or solvate thereof comprising: a matrix, wherein the matrix comprises a viscosity modifier in an amount from about 1 to about 60 percent by weight of the dosage form; and coated granules comprising said metoprolol or a pharmaceutically acceptable salt or solvate thereof; and wherein the matrix does not contain a lipid.

In another embodiment we provide an alcohol-resistant extended release dosage form for twice-daily administration of metoprolol or a pharmaceutically acceptable salt or solvate thereof comprising: a matrix, wherein the matrix comprises a viscosity modifier in an amount from about 1 to about 60 percent by weight of the dosage form; and coated granules comprising said metoprolol or a pharmaceutically acceptable salt or solvate thereof; and wherein the matrix does not contain a lipid.

Pharmaceutically acceptable salts of metoprolol, as used herein, can be any salts formed from the compound basic nitrogen atom and a suitable acid. Examples include, but are not limited to, tartrate, succinate and fumarate salts.

Pharmaceutically acceptable solvates of metoprolol, as used herein, include any metoprolol crystal that entraps solvents within the crystal structure that are generally referred to as solvent of crystallization. If the solvent is water, the formed crystalline material is referred to as hydrate; for other solvent the formed crystalline material is referred to as solvate. Other solvents include, but are not limited to, alcohols, ketones, esters, ethers hydrocarbon and fluorohydrocarbons.

Preferably, metoprolol is formulated according to the present invention as metoprolol tartrate or metoprolol succinate.

A viscosity modifier according to the invention can, for example, be selected from the group consisting of: sodium alginate, hydroxypropylmethylcellulose, hydroxyethylcellulose, hydroxypropylcellulose, methylcellulose, carboxymethylcellulose, sodium carboxymethylcellulose, crosslinked polyacrylic acid, gelatin, pectins, gums, polyethylene oxides, Konjac flour, carrageenan, xanthan gum, or mixtures thereof. For example, a viscosity modifier can be a gelling polymer, such as natural and synthetic starches, natural and synthetic celluloses, acrylates, and polyalkylene oxides. In some embodiments, the gelling polymer is selected from the group consisting of: hydroxypropylmethylcellulose, hydroxypropylcellulose, methylcellulose, hydroxyethylcellulose, and carboxymethylcellulose. For example, in some cases a gelling polymer can be hydroxypropylmethylcellulose.

In some embodiments, the viscosity modifier used in the matrix (hereinafter the "first viscosity modifier") is present in an amount from about 5 to about 45 percent by weight of the dosage form. In some embodiments, the first viscosity modifier is present in an amount from about 25 to about 45 percent by weight of the dosage form. In some embodiments, the first viscosity modifier is present in an amount from about 30 percent by weight of the dosage form.

A coated granule, as described herein, can comprise a granule comprising metoprolol or a pharmaceutically acceptable salt, or solvate thereof in an amount from about 10 to about 90 percent by weight of the granule, a first strong film former in an amount from about 1 to about 90 percent by weight of the granule, a second viscosity modifier in an amount from about 1 to about 90 percent by weight of the granule, and a fat/wax in an amount from about 0 to about 40 percent by weight of the granule; and a coating on the granule, wherein the coating is present in an amount from about 5 to about 70 percent by weight of the coated granule, and wherein the coating comprises a second strong film former in an amount from about 1 to about 50 percent by weight of the coated granule, and an anti-adherent in an amount from about 0 to about 30 percent by weight of the coated granule.

The first and second strong film formers can, for example, be independently selected from the group consisting of: natural and synthetic starches, natural and synthetic celluloses, acrylics, vinylics, resins, methacrylate or shellac. For example, the first and second strong film formers can be independently selected from the group consisting of: ethylcellulose; Ammonio Methacrylate Copolymer, Type B; Ammonio Methacrylate Copolymer, Type A; Amino Methacrylate Copolymer; Ethyl Acrylate and Methyl Methacrylate Copolymer Dispersion; Methacrylic Acid Copolymer, Type A; Methacrylic Acid Copolymer, Type B; and shellac. In some embodiments, the first strong film former and the second strong film former are the same. In some embodiments, the first and second strong film formers are ethylcellulose.

In some embodiments, the first strong film former is present in an amount from about 5 to about 40 percent by weight of the granule. For example, the first strong film former can be present in an amount from about 10 to about 30 percent by weight of the granule.

The second viscosity modifier can, for example, be selected from the same group as defined above for the first viscosity modifier. For example, the second viscosity modifier can be selected from the group consisting of: sodium alginate, hydroxypropylmethylcellulose, hydroxyethylcellulose, hydroxypropylcellulose, methylcellulose, carboxymethylcellulose, sodium carboxymethylcellulose, crosslinked polyacrylic acid, gelatin, pectins, gums, polyethylene oxides, Konjac flour, carrageenan, xanthan gum, or mixtures thereof.

In some embodiments, the second viscosity modifier is selected from the group consisting of: hydroxypropylmethylcellulose, hydroxypropylcellulose, methylcellulose, hydroxyethylcellulose, and carboxymethylcellulose. For example, the second viscosity modifier can be hydroxypropylmethylcellulose.

In some embodiments, the second viscosity modifier is present in an amount from about 1 to about 60 percent by weight of the granule. For example, the second viscosity modifier can be present in an amount from about 5 to about 30 percent by weight of the granule.

The fat/wax can be selected from the group of lipids that have melting point well above room temperature and typical storage condition (15-30° C.). Most preferably, the fat/wax can be selected from the group of lipids that has melting point above 60° C. Lipids with high melting point have improved stability and less susceptibility to gastric lipases which allows them to circumvent some of the disadvantage of using lipids described above. For example, the fat/wax can be independently selected from the group consisting of: glycerol behenate, carnauba wax and bees wax. In some embodiments, the fat/wax is glycerol behenate.

In some embodiments, the fat/wax is present in an amount from about 10 to about 25 percent by weight of the coated granule. In some embodiments, the granule does not contain a fat/wax.

In some embodiments, the coating contains a second strong film former in an amount from about 10 to about 50 percent by weight of the coated granule.

The anti-adherent can be a fat/wax as defined above or other agent that can prevent particle growth through agglomeration during coating. In one embodiment, suitable anti-adherents can be selected from a group of materials including stearic acid salts, talc, and starches. In some embodiments, the anti-adherent is magnesium stearate.

In some embodiments, metoprolol or a pharmaceutically acceptable salt or solvate thereof is present in an amount from about 30 to about 90 percent by weight of the granule. For example, the metoprolol and pharmaceutically acceptable salts thereof is present in an amount from about 50 to about 90 percent by weight of the granule.

The granules are coated and in some embodiments, the coating is present in an amount from about 30 to about 70 percent by weight of the coated granule. For example, the coating can be present in an amount from about 35 to about 55 percent by weight of the coated granule.

Also provided herein is an alcohol-resistant extended release oral dosage form comprising: a matrix, wherein the matrix comprises a first viscosity modifier in an amount from about 5 to about 45 percent by weight of the dosage form; and coated granules, wherein the coated granules comprise: a granule comprising metoprolol or a pharmaceutically acceptable salt, or solvate thereof in an amount from about 10 to about 90 percent by weight of the granule, a first strong film former in an amount from about 1 to about 90 percent by weight of the granule, a second viscosity modifier in an amount from about 1 to about 90 percent by weight of the granule, and a fat/wax in an amount from about 0 to about 40 percent by weight of the granule; and a coating on the granule, wherein the coating is present in an amount from about 5 to about 70 percent by weight of the coated granule, and wherein the coating comprises a second strong film former in an amount from about 1 to about 50 percent by weight of the coated granule, and an anti-adherent in an amount from about 0 to about 30 percent by weight of the coated granule; and wherein the matrix does not comprise a lipid.

In some cases, the dosage form can comprise a matrix, wherein the matrix comprises a first viscosity modifier in an amount from about 25 to about 45 percent by weight of the dosage form; and coated granules, wherein the coated granules comprise: a granule consisting essentially of metoprolol or a pharmaceutically acceptable salt, or solvate thereof in an amount from about 30 to about 90 percent by weight of the granule, a first strong film former in an amount from about 5 to about 40 percent by weight of the granule, a second viscosity modifier in an amount from about 1 to about 60 percent by weight of the granule, and a coating on the granule, wherein the coating is present in an amount from about 30 to about 70 percent by weight of the coated granule, and wherein the coating comprises a second strong film former in an amount from about 10 to about 50 percent by weight of the coated granule, and an anti-adherent in an amount from about 10 to about 25 percent by weight of the coated granule; and wherein the matrix does not comprise a lipid.

In some cases, the dosage form can comprise a matrix, wherein the matrix comprises hydroxypropylmethylcellulose in an amount from about 25 to about 45 percent by weight of the dosage form; and coated granules, wherein the coated granules comprise: a granule consisting essentially of metoprolol or a pharmaceutically acceptable salt or solvate thereof in an amount from about 50 to about 90 percent by weight of the granule, ethylcellulose in an amount from about 10 to about 30 percent by weight of the granule, hydroxypropylmethylcellulose in an amount from about 5 to about 30 percent by weight of the granule; and a coating on the granule, wherein the coating is present in an amount from about 30 to about 55 percent by weight of the coated granule, and wherein the coating comprises ethylcellulose in an amount from about 10 to about 50 percent by weight of the coated granule, and magnesium stearate in an amount from about 10 to about 25 percent by weight of the coated granule; and wherein the matrix does not comprise a lipid.

Further provided herein is a dosage form comprising: a matrix, wherein the matrix comprises hydroxypropylmethylcellulose in an amount of about 30 percent by weight of the dosage form; and coated granules, wherein the coated granules comprise: a granule consisting essentially of metoprolol succinate in an amount of about 70 to about 80 percent by weight of the granule, ethylcellulose in an amount from about 10 to about 20 percent by weight of the granule, and hydroxypropylmethylcellulose in an amount from about 5 to about 20 percent by weight of the granule; and a coating on the granule, wherein the coating is present in an amount from about 30 to about 55 percent by weight of the coated granule, and wherein the coating consists essentially of ethylcellulose in an amount from about 10 to about 50 percent by weight of the coated granule, and magnesium stearate in an amount from about 10 to about 25 percent by weight of the coated granule; and wherein the matrix does not comprise a lipid.

In some embodiments, the release of metoprolol succinate from a dosage form after 6 hours is less than about 80 percent when tested in 500 ml of 0.1N hydrochloric acid using USP dissolution apparatus. In some embodiments, the percent of a metoprolol released after 2 hours in a solution of 0.1N hydrochloric acid and 40% alcohol is no more than 10 percentage points greater than the percent of metoprolol released in a solution of 0.1N hydrochloric acid in the absence of alcohol. In some embodiments, the release of metoprolol hydrochloride from the dosage form 30 minutes after simulated oral tampering is less than about 50 percent.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a chart showing the comparative dissolution results for the marketed product Toprol XL in the absence and presence of 40% ethanol over a 6 hour period.

DETAILED DESCRIPTION

Figure 1:
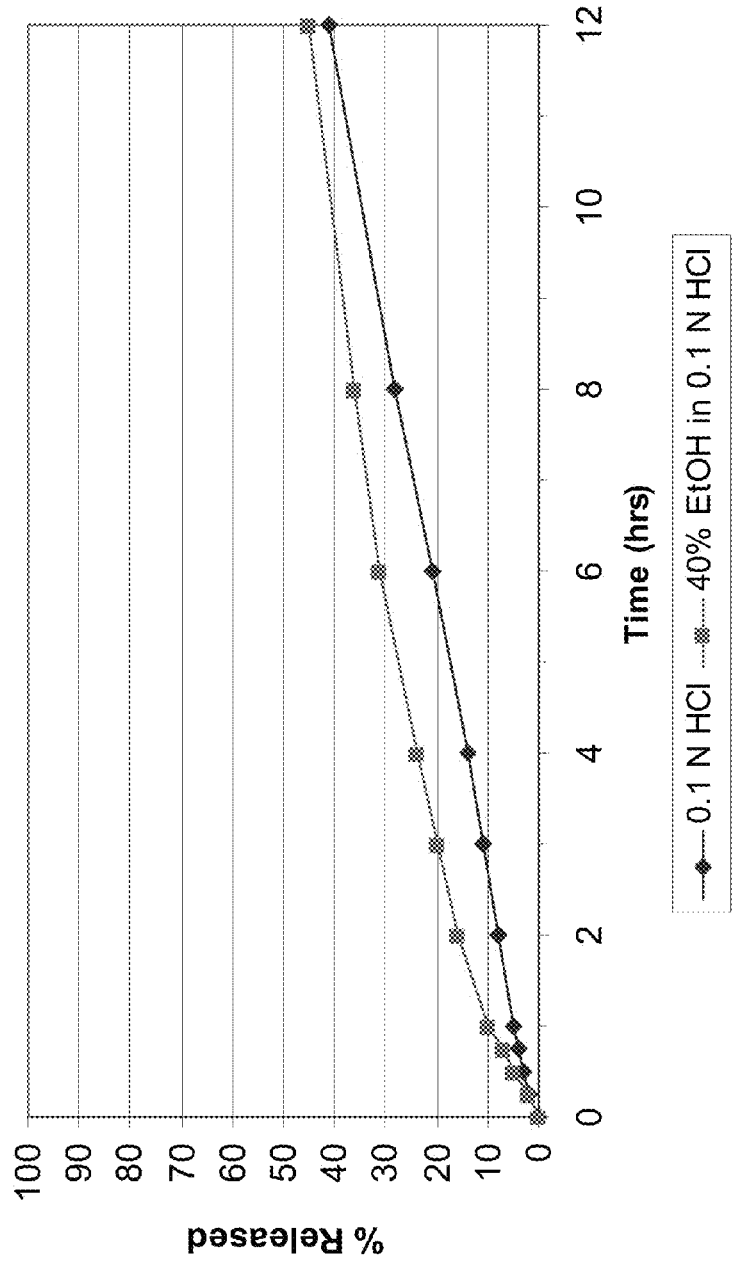
FIG. 1 is a chart showing the comparative dissolution results for the formulation product of Example 1 in the absence and presence of 40% ethanol over a 12 hour period.

Non-lipid matrix based alcohol-resistant extended release dosage forms of metoprolol and pharmaceutically acceptable salts and solvates thereof are provided. A dosage form can include a matrix having a viscosity modifier and coated granules comprising metoprolol or a pharmaceutically acceptable salt or solvate thereof. In some cases, a dosage form, as described herein, has a release profile such that after 6 hours in 500 ml of 0.1N hydrochloric acid, less than about 80 percent of the metoprolol is released. In addition, a dosage form may have crush resistance.

The term "matrix" refers to a monolithic system comprising active substance-containing particles (e.g., coated granules) dispersed and entrapped in a continuum of excipients, i.e., the "matrix forming" substances; see, for example, Colombo, P., Santi, P., Siepmann, J., Colombo, G., Sonvico, F., Rossi, A., Luca Strusi, O., 2008. Swellable and Rigid Matrices: Controlled Release Matrices with Cellulose Ethers. In: Pharmaceutical Dosage Forms: Tablets, Volume 2: Rational Design and Formulation. Third Edition, Augsburger, L. and Hoag, S. (eds.), Informa Healthcare, New York, London. As set forth further herein, coated granules comprising a metoprolol and pharmaceutically acceptable salts thereof are dispersed within a described matrix.

Provided herein is an extended release oral dosage form including a matrix, comprising a first viscosity modifier in an amount from about 5 to about 45 percent (e.g., about 25 to about 45 percent, including about 30 percent) by weight of the dosage form, and coated granules comprising metoprolol or a pharmaceutically acceptable salt or solvate thereof; and wherein the matrix does not comprise a lipid.

The dosage forms described herein can have a release profile such that the release of a metoprolol from the dosage form after 6 hours is less than about 80 percent. In some embodiments, the release of a metoprolol from the dosage form after 10 hours is less than about 85 percent. Release of metoprolol is measured using the USP dissolution apparatus number 2 and 500 ml of a 0.1N hydrochloric acid solution as the dissolution medium.

The dosage form is alcohol resistant. Resistance to alcohol is measured using the USP dissolution apparatus number 2 and 500 ml of a 0.1N hydrochloric acid solution (normal dissolution) or a 0.1N hydrochloric acid and 40% ethanolic solution (alcohol concentration is 40% v/v; dose dumping dissolution) as the dissolution medium. For an alcohol resistant formulation, as described herein, after 2 hours in a solution of 0.1N hydrochloric acid and 40% ethanol, the percent release of a metoprolol is no more than 10 percentage points greater than the percent of a metoprolol released in the 0.1N hydrochloric acid solution in the absence of alcohol. For example, if the dosage form releases 20% of the metoprolol in the 0.1N hydrochloric acid solution in the absence of alcohol after 2 hours, then an alcohol resistant dosage form, as described herein, will not release any more than 30% of the metoprolol in the solution having 0.1N hydrochloric acid and 40% ethanol.

In some embodiments, a dosage form, as described herein, may be crush resistant. Crush resistance is measured using techniques designed to simulate oral tampering. Such methods involve placing a tablet of the dosage form in a ceramic mortar (13 cm outer diameter). A pestle is then used to apply force vertically downward onto the tablet until it breaks. The broken tablet is further crushed using a 360° circular motion with downward force applied throughout. The circular crushing motion is repeated eleven times (twelve strokes total). The resulting powder is transferred to a dissolution vessel to measure in vitro drug release. The in vitro release profile of the crushed tablet samples is obtained in 500 ml of 0.1N hydrochloric acid dissolution medium. The samples are agitated at 50 rpm using USP apparatus 2 (paddles) at 37° C.

A viscosity modifier, as described herein, is a material, which upon dissolution or dispersion in an aqueous solution or dispersion (e.g., water) at a concentration of 2% w/w (based on the dry material), creates a solution/dispersion with a viscosity of from about 100 to about 200,000 mPa·s (e.g., 4,000 to 175,000 mPa·s, and 75,000 to 140,000 mPa·s) as measured at 20° C. (±0.2° C.) using the analysis method described in the USP 33 monograph for hypromellose (incorporated herein by reference). Examples of viscosity modifiers include sodium alginate, hydroxypropylmethylcellulose, hydroxyethylcellulose, hydroxypropylcellulose, carboxymethylcellulose, sodium carboxymethylcellulose, methylcellulose, crosslinked polyacrylic acid (e.g., carbomers), gelatin, pectins, gums (e.g., gum arabic, gum tragacanth, xanthan gums, and guar gums), polyethylene oxides, Konjac flour, carrageenan, or mixtures thereof. In some embodiments, the viscosity modifier is a natural or synthetic cellulose such as hydroxypropylmethylcellulose. In some embodiments, the viscosity modifier is a gelling polymer. Gelling polymers can include natural and synthetic starches, natural and synthetic celluloses, acrylates, and polyalkylene oxides. Examples include hydroxypropylmethylcellulose, hydroxypropylcellulose, methylcellulose, hydroxyethylcellulose, and carboxymethylcellulose. In some embodiments, the gelling polymer is hydroxypropylmethylcellulose (HPMC).

When HPMC is used in the dosage form, the HPMC can have different methyl to hydroxypropyl substitution percent ratios ranging from 30:0 in the A-type, 29:8.5 for the E-type, 28:5 in the F-type, 22:8 for the K-type all available from DOW Chemical Company, Midland, Mich. or any other HPMC polymers available from other suppliers such as Aqualon.

Coated granules of the dosage forms described herein include a granule comprising metoprolol or a pharmaceutically acceptable salt, or solvate thereof and a coating on the granule. In some embodiments, a coated granule can include a granule comprising metoprolol or a pharmaceutically acceptable salt, or solvate thereof in an amount from about 10 to about 90 percent by weight of the granule, a first strong film former in an amount from about 1 to about 90 percent by weight of the granule, a second viscosity modifier in an amount from about 1 to about 90 percent by weight of the granule, and a fat/wax in an amount from about 0 to about 40 percent by weight of the granule; and a coating on the granule, wherein the coating is present in an amount from about 5 to about 70 percent by weight of the coated granule, and wherein the coating comprises a second strong film former in an amount from about 1 to about 50 percent by weight of the coated granule, and an anti-adherent in an amount from about 0 to about 30 percent by weight of the coated granule.

In some embodiments, metoprolol or a pharmaceutically acceptable salt or solvate thereof is present in an amount from about 50 to about 90 percent by weight of the granule. In some embodiments, metoprolol or a pharmaceutically acceptable salt or solvate thereof is present in an amount from about 60 to about 90 percent by weight of the granule. In some embodiments, metoprolol succinate is present in an amount from about 70 to about 80 percent by weight of the granule.

A strong film former is a polymer, which is at least slightly soluble, preferably, soluble in alcohol and at most slightly soluble in water and forms a dry 3-mil film with tensile strength not less than 1000 lb/in$^2$ when measured by the appropriate tensile strength measuring equipment such as the texture analyzer manufactured by Texture Technologies, Brookfield, Lloyd Instruments, and the like. For example, a strong film former can be selected from natural and synthetic starches, natural and synthetic celluloses, acrylics, vinylics and resins. In some embodiments, a strong film former is selected from ethylcellulose; polyvinyl acetate; (meth)acrylate copolymers such as Ammonio Methacrylate Copolymer, Type B (Eudragit RS); Ammonio Methacrylate Copolymer, Type A (Eudragit RL); Amino Methacrylate Copolymer (Eudragit E); Ethyl Acrylate and Methyl Methacrylate Copolymer Dispersion (Eudragit NE); Methacrylic Acid Copolymer, Type A (Eudragit L); Methacrylic Acid Copolymer, Type B (Eudragit S); and shellac. In some cases, the first and second strong film formers are the same.

In some embodiments, a strong film former is a natural or synthetic cellulose such as ethylcellulose (EC). Ethylcellulose is an inert, hydrophobic polymer and is essentially tasteless, odorless, colorless, non-caloric, and physiologically inert. There are many types of ethylcellulose which can be used, as long as they meet the other requirements, such as alcohol solubility, discussed herein. The ethylcellulose used can have different ethoxy content such as 48.0-49.5% described as N-type; 49.6-51.5% described as T-type; 50.5-52.5% described as X-type; all available from Aqualon, Hercules Research Center, Wilmington, Del.

The ethylcellulose used can have different molecular weights such as including EC polymers of the N-type that form 5% w/w solution in toluene:ethanol (80:20) that have viscosity ranges of 5.6-8.0 centipoise (cps) described as N7; 8.0-11 cps described as N10; 12-16 cps described as N14; 18-24 cps described as N22; 40-52 cps described as N50; 80-105 cps described as N100. The ethylcellulose used can also include different degrees of substitution of ethoxy groups per anhydroglucose unit, such as 2.65-2.81 for the X-type. N-type has values of 2.46-2.58.

In some embodiments, the first strong film former is present in an amount from about 1 to about 90 percent by weight of the granule. For example, the first strong film former can be present in an amount from about 5 to about 40 percent by weight of the granule (e.g. from about 10 to about 30 percent by weight of the granule). In some cases, the second strong film former is present in an amount from about 10 to about 50 percent by weight of the coated granule. In some cases, the second strong film former can be present in an amount from about 10 to about 40 percent by weight of the coated granule.

In some embodiments, a second viscosity modifier is the same as the viscosity modifier used in the matrix of the dosage form. In some cases, the second viscosity modifier is hydroxypropylmethylcellulose. In some embodiments, the second viscosity modifier is present in an amount from about 1 to about 90 percent by weight of the granule. In some embodiments, the second viscosity modifier is present in an amount from about 1 to about 60 percent by weight of the granule, for example about 5 to about 40 percent by weight of the granule.

The lipid or fat/wax, as described herein, references to hydrophobic compounds generally having a hydrophilic/lipophilic balance (HLB) of about 6 or less and also having a melting point which is 30° C. or more. The term can be used interchangeably with fat or wax if they meet the same specifications. Lipids can be fatty acids, fatty alcohol, fatty esters or waxes. The fatty acids can be substituted or unsubstituted, saturated or unsaturated. However, generally they have a chain length of at least about 14. The fatty esters may include fatty acid bound to alcohols, glycols or glycerol to form mono-, di-, and tri-fatty substituted esters. Examples include, glycerol fatty esters, fatty glyceride derivatives, and fatty alcohols such as glycerol behenate (COMPRITOL®), glycerol palmitostearate (PRECIROL®), stearoyl macroglycerides (GELUCIRE®), insect and animal waxes, vegetable waxes, mineral waxes, petroleum waxes, and synthetic waxes.

The fat/wax, as used herein in the granules, can be independently selected from the group of lipids that have melting point well above room temperature and typical storage condition (15-30° C.). Most preferably, the fat/wax can be selected from the group of lipids that has melting point above 60° C. Lipids with high melting point have improved stability and less susceptibility to gastric lipases which allows them to circumvent the disadvantage of using lipids described above. For example, the fat/wax can be independently selected from the group consisting of: glycerol behenate, carnauba wax and bees wax. In some embodiments, the fat/wax are glycerol behenate.

In some cases, the fat/wax may be present in an amount from about 0 to about 30 percent by weight of the granule.

The coat may include anti-adherent which is used to prevent particle growth through agglomeration during coating. Anti-adherent can be selected from a fat/wax as defined hereinabove or a group of materials including stearic acid salts, talc, and starches. In some embodiment, the anti-adherent is magnesium stearate. In some embodiments, the anti-adherent is present in an amount from about 10 to about 25 percent by weight of the coated granule.

The term "coating" is meant to encompass a material which substantially surrounds the granules and provides some additional function, such as, without limitation, taste masking, storage stability, reduced reactivity, controlled release, and/or abuse resistance. In some embodiments, the coating is present in an amount from about 30 to about 70 percent by weight of the coated granule. For example, the coating can be present in an amount of about 30 to about 55 percent by weight of the coated granule, including about 35 to about 50 percent, e.g. about 40 to about 50 percent.

In some embodiments, the extended release oral dosage form described herein comprises a matrix, wherein the matrix comprises hydroxypropylmethylcellulose in an amount from about 5 to about 45 percent by weight of the dosage form, for example, from about 25 to about 45 percent by weight, including about 30 percent by weight, of the dosage form; and coated granules, wherein the coated granules comprise a granule comprising metoprolol or a pharmaceutically acceptable salt thereof in an amount from about 50 to about 90 percent by weight of the granule, for example, from about 60 to about 90 percent by weight of the granule, ethylcellulose in an amount from about 5 to about 40 percent by weight of the granule, for example, from about 10 to about 30 percent by weight of the granule, hydroxypropylmethylcellulose in an amount from about 1 to about 60 percent by weight of the granule, for example, from about 5 to about 20 percent by weight of the granule, and a fat/wax (e.g. glycerol behenate) in an amount from about 0 to about 20 percent by weight of the granule; and a coating on the granule, wherein the coating is present in an amount from about 5 to about 70 percent by weight of the coated granule, for example, in an amount of about 30 to about 70 percent by weight of the coated granule, including about 30 to about 55 percent, e.g. about 40 percent, and wherein the coating comprises ethylcellulose in an amount from about 1 to about 50 percent by weight of the coated granule or from about 10 to about 40 percent by weight of the coated granule, and magnesium stearate in an amount from about 10 to about 25 percent by weight of the coated granule; and wherein the matrix does not comprise a lipid.

In some embodiments, the extended release oral dosage form described herein comprises a matrix, wherein the matrix comprises hydroxypropylmethylcellulose in an amount from about 5 to about 45 percent by weight of the dosage form, for example, from about 25 to about 45 percent by weight, including about 30 percent by weight, of the dosage form; and coated granules, wherein the coated granules comprises a granule consisting essentially of metoprolol or a pharmaceutically acceptable salt, or solvate thereof in an amount from about 50 to about 90 percent by weight of the granule, for example, from about 60 to about 90 percent by weight of the granule, ethylcellulose in an amount from about 5 to about 40 percent by weight of the granule, for example, from about 10 to about 30 percent by weight of the granule, hydroxypropylmethylcellulose in an amount from about 1 to about 60 percent by weight of the granule, for example, from about 5 to about 20 percent by weight of the granule, and a fat/wax (e.g. glycerol behenate) in an amount from about 0 to about 20 percent by weight of the granule; and a coating on the granule, wherein the coating is present in an amount from about 5 to about 70 percent by weight of the coated granule, for example, in an amount of about 30 to about 70 percent by weight of the coated granule, including about 30 to about 55 percent, e.g. about 40 percent, and wherein the coating comprises ethylcellulose in an amount from about 1 to about 50 percent by weight of the coated granule or from about 10 to about 40 percent by weight of the coated granule, and magnesium stearate in an amount from about 10 to about 25 percent by weight of the coated granule; and the matrix does not comprise a lipid.

In some embodiments, the extended release oral dosage form described herein comprises a matrix, wherein the matrix comprises hydroxypropylmethylcellulose in an amount from about 5 to about 45 percent by weight of the dosage form, for example, from about 25 to about 45 percent by weight, including about 30 percent by weight, of the dosage form; and coated granules, wherein the coated granules comprise a granule consisting essentially of metoprolol or a pharmaceutically acceptable salt, or solvate thereof in an amount from about 50 to about 90 percent by weight of the granule, for example, from about 60 to about 90 percent by weight of the granule, ethylcellulose in an amount from about 5 to about 40 percent by weight of the granule, for example, from about 10 to about 30 percent by weight of the granule, hydroxypropylmethylcellulose in an amount from about 1 to about 60 percent by weight of the granule, for example, from about 5 to about 20 percent by weight of the granule, and a fat/wax (e.g. glycerol behenate) in an amount from about 0 to about 20 percent by weight of the granule; and a coating on the granule, wherein the coating is present in an amount from about 5 to about 70 percent by weight of the coated granule, for example, in an amount of about 30 to about 70 percent by weight of the coated granule, including about 30 to about 55 percent, e.g. about 40 percent, and wherein the coating consists essentially of ethylcellulose in an amount from about 1 to about 50 percent by weight of the coated granule or from about 10 to about 40 percent by weight of the coated granule, and magnesium stearate in an amount from about 10 to about 25 percent by weight of the coated granule; and the matrix does not comprise a lipid.

In some embodiments, the extended release oral dosage form described herein comprises a matrix, wherein the matrix comprises hydroxypropylmethylcellulose in an amount from about 30 percent by weight of the dosage form; and coated granules, wherein the coated granules comprise a granule consisting essentially of metoprolol succinate in an amount from about 70 to about 80 percent by weight of the granule, ethylcellulose in an amount from about 10 to about 20 percent by weight of the granule, hydroxypropylmethylcellulose in an amount from about 5 to about 20 percent by weight of the granule; and a coating on the granule, wherein the coating is present in an amount from about 30 to about 55 percent, e.g. about 50 percent, and wherein the coating consists essentially of ethylcellulose in an amount from about 10 to about 40 percent by weight of the coated granule, and magnesium stearate in an amount from about 10 to about 25 percent by weight of the coated granule; and the matrix does not comprise a lipid.

The coated granules and dosage forms as described herein can be prepared using methods known to those in the art, see, for example, U.S. Publication No. 2008/0311205, incorporated herein by reference. In general, the high water-soluble high dose drug is formulated into polymer-rich granules onto which a polymeric coat is applied. The coated granules are subsequently mixed with a viscosity modifier.

In some embodiments, the dosage form may also include at least one other ingredient or excipient in addition to the coated particle and viscosity modifier in the matrix. The other ingredient or excipient may include, but is not limited to, taste masking agents, binders, fillers, sugars, artificial sweeteners, polymers, flavoring agents, coloring agents, lubricants, glidants, bio- or muco-adhesives, surfactants, buffers, and disintegrants. The amount of any one or more of these ingredients will vary with the amount of coating, granule size, shape of the dosage form, form of the dosage form, number of ingredients used, the particular mixture of ingredients used, the number of dosage forms that will formulate a dose, the amount of drug per dose and the like. Any combination or amounts are contemplated sufficient to produce a dosage form having the described release profile and/or tamper-resistance provided.

"Taste masking agent(s)" include anything known to be used as a taste masking agents in this art. Examples include Eudragit E-100, ethylcellulose, hydroxypropylmethylcellulose, hydroxypropyl cellulose, methylcellulose, Hydroxyethylcellulose, carboxymethylcellulose, shellac, zein, carbomers, poloxamers, modified chitosans, carrageenans, cellulose acetate trimellitate, hydroxypropyl methylcellulose phthalate, hydroxypropylmethylcellulose acetate succinate, methacrylic acid copolymers including Eudragit L 100, S 100, L30D-55, polyvinylacetate phthalate (PVAP). Taste masking agents can be used in conventional amounts, for example, in an amount of about 0 to about 50 percent by weight of the total dosage form (e.g., about 5 to about 40 percent by weight of the total dosage form; about 10 to about 30 percent by weight of the total dosage form).

Binders can be used to add cohesiveness to powders and provide the necessary bonding to form granules that can be compressed into hard tablets that have acceptable mechanical strength to withstand subsequent processing or shipping and handling. Examples of binders include acacia, tragacanth, gelatin, starch (both modified or unmodified), cellulose materials such as methylcellulose, ethylcellulose, hydroxypropylmethylcellulose, hydroxypropylcellulose, hydroxyethylcellulose and sodium carboxy methylcellulose, alginic acids and salts thereof, magnesium aluminum silicate, polyethylene glycol, guar gum, polysaccharide acids, bentonites, sugars, invert sugars, and the like, polyvinylpyrrolidone, polymethacrylate and other acrylic and vinyl-based polymers. Binders can be used in a conventional amount, for example, in an amount of about 0 to about 50 percent by weight of the total dosage form (e.g., about 2 to about 10 percent by weight of the total dosage form).

Fillers can include mannitol, dextrose, sorbitol, lactose, sucrose, and calcium carbonate. Fillers can be used in a conventional amount, for example, in an amount of about 0 to about 90 percent by weight of the total dosage form (e.g., from about 10 to about 50 percent by weight of the total dosage form). In some embodiments, a filler can be a sugar. For example, sugar, sugar alcohols, ketoses, saccharides, polysaccharides, oligosaccharides and the like, as well as celluloses and modified celluloses.

Sugars may also include direct compression and/or non-direct compression sugars. Non-direct compression sugars include, without limitation, dextrose, mannitol, sorbitol, trehalose, lactose and sucrose. These sugars generally exist as either a direct compression sugar, i.e., a sugar which has been modified to increase its compressibility and/or flow, or a non-direct compression sugar which does not have sufficient flowability and/or compressibility to allow it to be used in high speed processing and multi-tablet presses without some sort of augmentation such as, without limitation, a glidant to increase flow, granulation to increase flow and/or compressibility and the like. While not definitive, sometimes a non-direct compression sugar will have at least about 90% of its particles smaller than about 200 microns, and more preferably 80% smaller than about 150 microns.

The amount of total sugar can range from about 0 to about 90 (e.g., about 5 to about 75; about 10 and 50) by weight of the total dosage form. Other non-carbohydrate diluents and fillers which may be used include, for example, dihydrated or anhydrous dibasic calcium phosphate, tricalcium phosphate, calcium carbonate, anhydrous or hydrated calcium sulphate, and calcium lactate trihydrate. Non-carbohydrate diluents and fillers may be used in an amount of from about 0 to about 90 percent (e.g., from about 5 to about 75 percent; from about 10 to about 50 percent) by weight of the total dosage form.

Artificial sweeteners can include saccharin, aspartame, sucralose, neotame, and acesulfame potassium. Artificial sweeteners may be used in conventional amounts, for example, in an amount ranging from about 0.1 to about 2 percent by weight of the total dosage form.

Flavoring agents can include synthetic flavor oils and flavoring aromatics and/or natural oils, extracts from plants, leaves, flowers, fruits and so forth and combinations thereof.

For example, cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavoring agents are vanilla, citrus oil, including lemon, orange, banana, grape, lime and grapefruit, and fruit essences, including apple, pear, peach, strawberry, raspberry, cherry, plum, pineapple, apricot and so forth.

Flavoring agents may be used in conventional amounts, for example, in an amount ranging from about 0.01 to about 3 percent by weight of the dosage form (e.g., from about 0.1 to about 2.5 percent by weight of the dosage form; from about 0.25 to about 2 percent by weight of the dosage form).

Coloring agents can include titanium dioxide, iron oxides such as red or yellow iron oxide, and dyes suitable for food such as those known as FD&C dyes and natural coloring agents such as grape skin extract, beet red powder, beta-carotene, annatto, carmine, turmeric, and paprika. Coloring agents may be used in conventional amounts, for example, in an amount ranging from about 0.001 to about 1% by weight of the total dosage form.

Lubricants can include intrinsic or extrinsic lubricants. Intrinsic lubricants may include magnesium, calcium, zinc salts of stearic acid, hydrogenated and partially hydrogenated vegetable oils, animal fats, polyethylene glycol, polyoxyethylene monostearate, talc, light mineral oils, sodium benzoate, sodium lauryl sulphate, magnesium oxide and the like. Lubricants may be used in conventional amounts, for example, in an amount from about 0.1 to about 5 percent by weight of the dosage form (e.g., from about 0.25 to about 2.5 percent; from about 0.5 to about 2 percent).

Surfactants can include, without limitation, various grades of the following commercial products: Arlacel®, Tween®, Capmul®, Centrophase®, Cremophor®, Labrafac®, Labrafil®, Labrasol®, Myverol®, Tagat®, and any non-toxic short and medium chain alcohols. Surfactants can be used in conventional amounts, for example, in an amount of about 0.01 to about 5 percent by weight of the dosage form (e.g., in an amount of about 0.1 to about 2 percent).

Buffers can include any weak acid or weak base or, preferably, any buffer system that is not harmful to the gastrointestinal mucosa. These include, but are not limited to, sodium carbonate, potassium carbonate, potassium carbonate, disodium hydrogen phosphate, sodium dihydrogen phosphate, and the equivalent potassium salts. Buffers can be used in conventional amounts, for example, in an amount of about 0.1 to about 10 percent by weight of the dosage form (e.g., from about 1 to about 5 percent).

The dosage form may also contain minor amounts of nontoxic substances such as wetting or emulsifying agents, pH buffering agents and the like, for example, sodium acetate, sorbitan monolaurate, triethanolamine, sodium acetate, triethanolamine oleate, sodium lauryl sulfate, dioctyl sodium sulfosuccinate, polyoxyethylene sorbitan fatty acid esters.

A "dosage form", as used herein, is a tablet, capsule, caplet, sachet, powder or other solid known for the administration of medicines orally. It is generally made from a mixture as defined herein and is generally formed (as in a tablet) into a form for use by a doctor or patient for administration.

Dosage forms may be provided in a range of shapes and sizes. In some embodiments, the dosage form is in a size capable of oral administration and provides a therapeutic amount of drug. Generally, such dosage forms will be less than 1.5 inches in any one direction, more preferably less than 1 inch and most preferably less than 0.75 inch. Shapes include but not limited to round with both flat or convex face, capsule shape (caplets), diamond shape, triangular, rectangular, hexagonal, pentagonal, heart-shaped, animal shaped tablets like rabbits, elephants etc. Dosage forms can be any size and shape, but preferable of a size and shape to maximize alcohol resistance.

Dosage forms, especially tablets, may also be coated to improve the appearance of the dosage form, and also to maximize alcohol resistance.

Dosage forms are formulated to be suitable generally for once-a-day or twice-a-day administration. The amount of drug present in the dosage form can vary from about 1 mg to 1000 mg, more preferably 10 mg to 800 mg and most preferably 25 mg to 400 mg.

Tablets can either be manufactured by direct compression, wet granulation, dry granulation followed by coating and tablet compression or any other tablet manufacturing technique. See, e.g., U.S. Pat. Nos. 5,178,878, 5,223,264 and 6,024,981 which are incorporated by reference herein.

EXAMPLES

Example 1

190 mg Metoprolol Succinate Formulation
(Equivalent to 200 mg Metoprolol Tartrate)

TABLE 1

| Material | % w/w |
|---|---|
| Uncoated Granules | |
| Metoprolol succinate | 76.8 |
| hydroxypropylmethylcellulose (K100M) | 9.6 |
| ethylcellulose | 13.6 |
| Coated Granules | |
| uncoated granules | 60.00 |
| ethylcellulose | 26.7 |
| magnesium stearate | 13.3 |
| Dosage Form | |
| coated granules | 48.5 |
| lactose monohydrate | 21.0 |
| hydroxypropylmethylcellulose (K100M) | 30.0 |
| magnesium stearate | 0.5 |

Granules were manufactured in a high shear granulator where Metoprolol succinate, hydroxypropylmethylcellulose and a portion of the ethylcellulose were dry mixed for 2 minutes. Then, a 10% hydro-ethanolic (30:70) solution of the remaining ethylcellulose was slowly added while maintaining the granulator impeller and chopper speeds at pre-selected values to provide enough shear for granule formation and growth. Solution addition was continued until the aforementioned percentage of ethylcellulose was realized. The granules were then milled in a granumill and finally dried.

The uncoated granules were then coated in a bottom spray fluid bed using a 15% acetone suspension of a 2:1 ethylcellulose/magnesium stearate mixture to provide a coat of 40% by weight of the coated granules. Coated granules were mixed with lactose monohydrate and hydroxypropylmethylcellulose in a V-blender for a period of about 30 minutes. Magnesium stearate was added and the mixture blended for an additional 5 minutes. The amount of coated granules charged into the tablet is based on the actual coated granule content of Metoprolol succinate; it is not based on the theoretical content. The blended mixture was then compressed in a rotary tablet press to form tablets. The 0.3125×0.5625 inch capsule shaped tablets weighed 850 mg and had an average hardness of about 111 N.

Example 2

Dissolution and Tamper Testing

The product of Example 1 was subjected to dissolution experiments in 0.1N hydrochloric acid and 0.1N hydrochloric acid and 40% v/v alcohol. Tablets were tested using the USP dissolution apparatus number 2 using 500 ml of 0.1N hydrochloric acid (normal dissolution) or 40% ethanolic solution (dose dumping dissolution) as the dissolution medium. Unless otherwise specified, aliquots were removed after 15, 30, 45, 60, 120, 180, 240, 480, 720 minutes of stirring in the normal dissolution test and the dose dumping dissolution. Samples were analyzed for drug using HPLC.

Results of the above experiments are detailed in FIG. 1. Tablets were considered to be alcohol-resistant if the percent of drug released after 2 hours in 0.1N hydrochloric acid/40% v/v alcohol was no more than 10 percentage points greater than the percent of drug released after 2 hours from a solution of 0.1N hydrochloric acid in the absence of alcohol.

As seen in FIG. 1, the formulated dosage form met the criteria for alcohol resistance. Specifically, for the metoprolol succinate formulated product, the percent of drug released after 2 hours in absence of alcohol was 8% compared to 16% in presence of alcohol. The drug release in alcohol was extended over 12 hours reflecting protection against alcohol is extended well beyond the 2 hours described above. The results are in contrast to the commercially available metoprolol succinate products known as Toprol XL. The results for this product are shown in FIG. 2. As seen in the figure the product was very susceptible to alcohol with 90% of the dose released in the presence of alcohol compared to 21% released in absence of alcohol after 2 hours.

Simulated oral tampering testing is conducted by crushing tablets using ceramic mortars and pestles. A tablet is placed in a ceramic mortar (13 cm outer diameter). A pestle is used to apply force vertically downward onto the tablet until it breaks. The broken tablet is further crushed using a 360° circular motion with downward force applied throughout. The circular crushing motion is repeated eleven times (twelve strokes total). The resulting powder is transferred to a dissolution vessel for in vitro drug release. The in vitro release profile of the crushed tablet samples is obtained in 500 mL of 0.1N hydrochloric acid dissolution medium. The samples are agitated at 50 rpm with USP apparatus 2 (paddles) at 37° C. These are the same in vitro conditions as those employed in the in vitro dissolution test described above. Aliquots are removed after 15, 30, 45, 60, and 120 minutes of stirring and are analyzed for drug using HPLC.

A number of embodiments of the invention have been described. Nevertheless, it will be understood that various modifications may be made without departing from the spirit and scope of the invention. Accordingly, other embodiments are within the scope of the following claims.

What is claimed is:

1. An extended release oral dosage form comprising:
   a matrix, wherein the matrix comprises a gelling polymer in an amount from about 25 to about 45 percent by weight of the dosage form, wherein the matrix does not contain a lipid; and
   coated granules, wherein the coated granules comprise
   a granule, comprising:
   metoprolol or a pharmaceutically acceptable salt or solvate thereof in an amount from about 10 to about 90 percent by weight of the granule,
   ethyl cellulose in an amount from about 10 to about 30 percent by weight of the granule, and
   a viscosity modifier in an amount from about 5 to about 30 percent by weight of the granule; and
   a fat/wax selected from: glycerol fatty esters and waxes and present in an amount from about 0 to about 40 percent by weight of the granule; and
   a coating on the granule, wherein the coating is present in an amount from about 35 to about 55 percent by weight of the coated granule, and wherein the coating comprises ethyl cellulose in an amount from about 1 to about 50 percent by weight of the coated granule, and an antiadherent in an amount from about 0 to about 30 percent by weight of the coated granule
   wherein the gelling polymer in the matrix is selected from hydroxypropylmethylcellulose, hydroxypropylcellulose, methylcellulose, hydroxyethylcellulose, and carboxymethylcellulose, and
   wherein the viscosity modifier in the granule is selected from sodium alginate, hydroxypropylmethylcellulose, hydroxyethylcellulose, hydroxypropylcellulose, methylcellulose, carboxymethylcellulose, sodium carboxymethylcellulose, crosslinked polyacrylic acid, gelatin, pectins, gums, polyethylene oxides, Konjac flour, carrageenan, xanthan gum, or mixtures thereof.

2. An oral dosage form according to claim 1, wherein the percent of metoprolol released after 2 hours in a solution of 0.1N hydrochloric acid and 40% alcohol is no more than 10 percentage points greater than the percent of said metoprolol released in a solution of 0.1N hydrochloric acid in the absence of alcohol.

3. An oral dosage form according to claim 1, wherein the release of metoprolol from the dosage form 6 hours after testing is less than about 80 percent when tested in 500 ml of 0.1N hydrochloric acid solution using USP dissolution apparatus.

4. The dosage form of claim 1, wherein the viscosity modifier in the granule is hydroxypropylmethylcellulose.

5. The dosage form of claim 1, wherein the fat/wax is glycerol behenate.

\* \* \* \* \*